United States Patent [19]

Moore

[11] Patent Number: 4,524,210

[45] Date of Patent: Jun. 18, 1985

[54] 2,6-DI(T-BUTYL)-4-HYDROXY-4-PYRIDYL-2,5-CYCLOHEXADIEN-1-ONE INTERMEDIATES

[75] Inventor: George G. I. Moore, Houlton, Wis.

[73] Assignee: Riker Laboratories, Inc., St. Paul, Minn.

[21] Appl. No.: 522,386

[22] Filed: Aug. 12, 1983

Related U.S. Application Data

[62] Division of Ser. No. 324,062, Nov. 23, 1981, Pat. No. 4,414,217.

[51] Int. Cl.³ .......................................... C07D 213/04
[52] U.S. Cl. .................................... 546/340; 556/486
[58] Field of Search ......................................... 546/340

[56]  References Cited

U.S. PATENT DOCUMENTS

| | | | |
|---|---|---|---|
| 4,026,900 | 5/1977 | Gelotte et al. | 546/340 |
| 4,124,725 | 11/1978 | Moore | 424/330 |
| 4,128,664 | 12/1978 | Moore | 424/324 |
| 4,172,082 | 10/1979 | Moore | 549/72 |
| 4,172,151 | 10/1979 | Moore | 424/330 |

Primary Examiner—Jane T. Fan
Attorney, Agent, or Firm—Donald M. Sell; James A. Smith; Robert W. Sprague

[57] ABSTRACT 3,5-Di(t-butyl)-4-hydroxyphenyl and 3,5-di(t-butyl)-4-hydroxybenzoyl-substituted pyridines have pharmacological activity as antiinflammatory agents.

2 Claims, No Drawings

2,6-DI(T-BUTYL)-4-HYDROXY-4-PYRIDYL-2,5-CYCLOHEXADIEN-1-ONE INTERMEDIATES

This is a division of application Ser. No. 324,062 filed Nov. 23, 1981, now U.S. Pat. No. 4,414,217.

TECHNICAL FIELD

This invention relates to certain substituted pyridine compounds, to the use of such compounds as antiinflammatory agents, and to novel intermediates useful for preparing final product compounds of the invention.

BACKGROUND ART

I have previously synthesized and described several antiinflammatory compounds containing di(t-butyl)-phenol groups. Information regarding these compounds is contained in U.S. Pat. Nos. 4,128,664 (2,6-di(t-butyl)-phenol substituted in the 4-position by an N-substituted carboxamido group), 4,124,725 (2,6-di(t-butyl)phenol substituted in the 4-position by an optionally substituted benzoyl group), 4,172,151 (2,6-di(t-butyl)phenol substituted in the 4-position by an optionally substituted phenyl group), and 4,172,082 (2,6-di(t-butyl)phenol substituted in the 4-position with optionally substituted thiophenyl groups).

DISCLOSURE OF INVENTION

The above described compounds are antiinflammatory agents useful in the treatment of inflammation related conditions such as rheumatoid arthritis. Many of the above compounds also have activity as stabilizers against oxidation, and this characteristic may be related to the efficacy of the above compounds as antiinflammatory agents, although there is no present confirmation of this possibility. The 3,5-di(t-butyl)-4-hydroxyphenyl moiety found in each of the above compounds is also found in the well-known antioxidant 3,5-di(t-butyl)-4-hydroxytoluene (commonly referred to as butylated hydroxytoluene, or "BHT"), a substance which is frequently used as a food additive to extend the shelf life of processed foods. BHT itself has little or no pharmacological value as an antiinflammatory agent. Likewise, many other compounds containing groups derived from di(t-butyl)phenol have little or no pharmacological value, e.g., 2,6-di(t-butyl)phenol, 4-carbox-amido-2,6-di(t-butyl)phenol, 4-(2-chlorobenzoyl)-2,6-di(t-butyl)phenol, 4-(5-carboxy-2-thenoyl)-2,6-di(t-butyl)phenol, 2,6-di(t-butyl)-4-phenylsulfonylphenol, 4-acetyl-2,6-di(t-butyl)phenol, and 4-n-octyl-2,6-di(t-butyl)phenol.

Compounds other than those already described in the above-mentioned patents containing 3,5-di(t-butyl)-4-hydroxyphenyl groups may also have pharmacological activity as antiinflammatory agents. However, at the present time there appear to be no rules by which one could correlate structural similarities between various compounds containing the 3,5-di(t-butyl)-4-hydroxyphenyl moiety with the presence of useful antiinflammatory activity in such compounds. New antiinflammatory compounds containing the 3,5-di(t-butyl)-4-hydroxyphenyl moiety must be discovered by trial and error synthesis and testing.

The present invention provides, in one aspect, compounds of the formula:

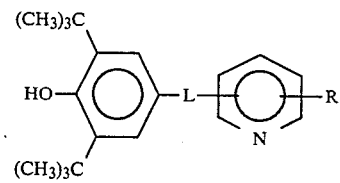

wherein L is a carbon-carbon bond or a carbonyl radical and R is hydrogen or methyl, with the proviso that when L is a carbonyl radical bonded to the 2-position of the pyridine ring and R is methyl, R is bonded to the 3- or 5-position of the pyridine ring. The present invention also provides quaternary ammonium salts of the compounds of Formula I. In addition, the present invention provides antiinflammatory compositions containing such compounds and salts, methods for combatting inflammatory reactions in mammals, and novel intermediates useful for preparing such compounds and salts.

DETAILED DESCRIPTION

In the practice of the present invention, compounds wherein L is a carbon-carbon bond are prepared by the reaction of 2,6-di(t-butyl)benzoquinone with an organometallic reagent such as pyridyl lithium or pyridyl magnesium halide (Process A). Such organometallic reagents are generally prepared from halogenated pyridines. Halogenated pyridines are known to the art, as are procedures for their preparation. Among the known halogenated pyridines are 3-bromopyridine, 2-iodopyridine, 2-bromopyridine, 2-chloropyridine, 3-chloropyridine, 3-iodopyridine, and the like.

Such reactions between the magnesium or lithium reagents of pyridine and 2,6-di(t-butyl)benzoquinones provide the intermediate optionally substituted 2,6-di(t-butyl)-4-hydroxy-4-pyridyl-2,5-cyclohexadien-1-ones having the formula:

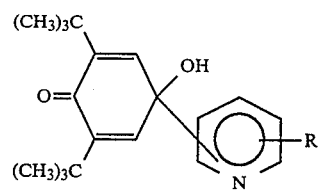

wherein R is as defined above for Formula I. These compounds (Formula II) are novel and fall within the scope of the present invention. They are reduced to form compounds of Formula I, using hydrogen gas with a catalyst such as palladium on charcoal or Raney nickel, or by using a metal hydride reducing agent such as lithium aluminum hydride, or by using hydrogen iodide.

An alternative method for making 2-pyridyl compounds is the thermal decomposition of picolinic acid (Process B). This can be carried out by heating picolinic acid and 2,6-di(t-butyl)benzoquinone in cymene, followed by extraction and evaporation to provide an intermediate corresponding to Formula II above.

The compounds of the invention wherein L is a carbonyl radical are prepared by several methods. In general, these methods involve the reaction of 2,6-di(t-butyl)-4-bromophenol derivatives with various substituted pyridines. The various methods can be illustrated as follows:

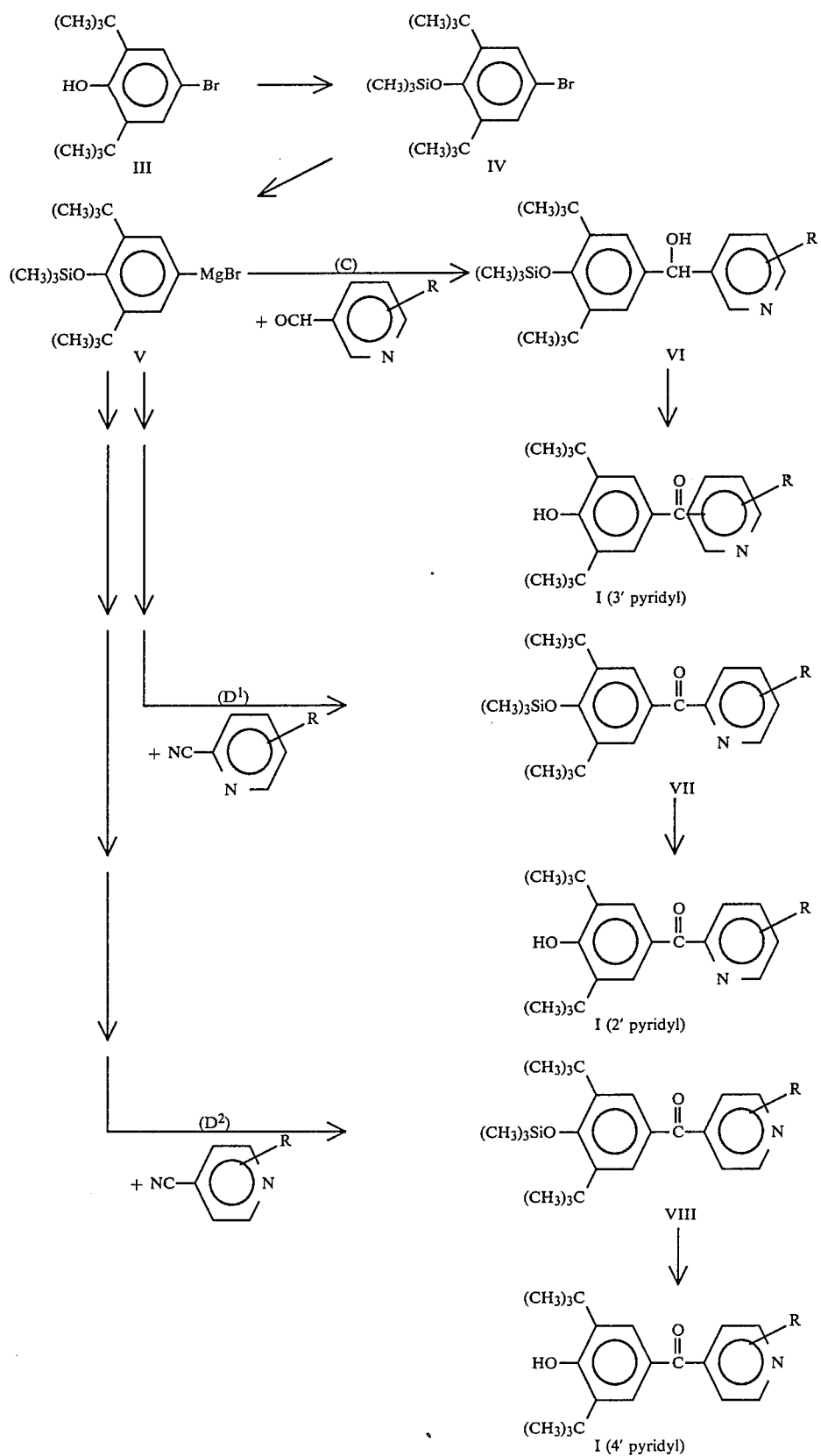
In the reaction sequence shown above, 2,6-di(t-butyl)-4-bromophenol (Formula III) is converted to the novel intermediate 2,6-di(t-butyl)-4-bromotrimethylsiloxyphenol (Formula IV) by reaction with trimethylsilyl chloride or bis(trimethylsilyl)acetamide. This reaction sequence lessens the likelihood that side reactions will take place. The reaction with trimethylsilyl chloride is carried out by reacting the compound of Formula III with an equimolar amount of a strong base such as sodium methoxide or n-butyl lithium under mild conditions. The resulting phenoxide is reacted with trimethylsilyl chloride to form the compound of Formula IV. As an alternate route the compound of Formula III is reacted directly with bis(trimethylsilyl)acetamide and acetonitrile to form the compound of Formula IV.

The bromo group of the novel compound of Formula IV is readily reacted to provide the corresponding novel Grignard reagent of Formula V. This Grignard reagent is then further reacted to provide the desired end product, as described below.

For compounds of the invention wherein the 2,6-di(t-butyl)phenol group is linked by a carbonyl radical to the 3-position of an optionally substituted pyridine ring, it is preferred to react the Grignard reagent of Formula V with a pyridine-3-carboxaldehyde (Process C). The resulting novel intermediate of Formula VI contains a 3-pyridyl group linked by a hydroxymethylene radical to a 2,6-di(t-butyl)trimethylsiloxyphenyl group. This reaction sequence will also work with pyridine-2- or -4-carboxaldehydes. The intermediate of Formula VI is then oxidized and hydrolyzed to a compound of the invention of Formula I wherein L is a carbonyl radical. The oxidation is carried out, for example, by heating the intermediate of Formula VI with sodium dichromate and sulfuric acid in dimethyl sulfoxide.

Suitable intermediate pyridine-3-carboxaldehydes for use in the above synthetic sequence are known, e.g., pyridine-3-carboxaldehyde, 4-methylpyridine-3-carboxaldehyde, and the like.

For compounds of the invention wherein the 2,6-di(t-butyl)phenol group is linked by a carbonyl radical to the 2- or 4-positions of an optionally substituted pyridine ring, it is preferred to react the Grignard reagent (III) with a 2- or 4-cyanopyridine by refluxing in an inert solvent such as tetrahydrofuran (Processes $D^1$ and $D^2$), yielding the trimethylsilyl compounds VII or VIII. The trimethylsilyl group is removed by hydrolysis in aqueous acid, e.g., ten percent hydrochloric acid.

Suitable intermediate 2- and 4-cyanopyridines for use in the above synthetic sequence are known, e.g., 2-cyanopyridine, 4-cyanopyridine, 3-methyl-2-cyanopyridine, 5-methyl-2-cyanopyridine, and the like.

Quaternary ammonium salts of the compounds of the invention can be formed by reaction of the pyridyl nitrogen with a reactive alkyl halide such as an alkyl bromide or iodide in a suitable non-reactive solvent such as an alkanol, e.g., ethanol. Preferred quaternary ammonium salts are prepared from lower ($C_{1-6}$) alkyl bromides and iodides.

Preferred compounds of the invention are 2,6-di(t-butyl)-4-nicotinoylphenol, 2,6-di(t-butyl)-4-(2'-pyridinecarbonyl)phenol, 2,6-di(t-butyl)-4-(3'-methyl-2'-pyridinecarbonyl)phenol, and 2,6-di(t-butyl)-4-(2'-pyridyl)phenol, and the preparation of these compounds is described below in Examples 1, 3, 4, and 7, respectively.

In addition to their use as effective antiinflammatory agents, the compounds of the invention are relatively active as stabilizers to prevent oxidation. Some also are analgesics, some are antipyretic agents, and some have mild immunosuppressant activity.

In order to determine and assess pharmacological activity, testing in animals is carried out using various assays known to those skilled in the art. Thus, the antiinflammatory activity of compounds of the invention can be conveniently demonstrated using an assay designed to measure the ability of these compounds to inhibit the enzyme prostaglandin synthetase (cyclooxygenase), such as the test described in White and Glossman, *Prostaglandins*, 7, 123 (1974). The antiinflammatory activity of the compounds of the invention can also be demonstrated using an assay designed to test the ability of these compounds to antagonize the local edema which is characteristic of the inflammatory response (the rat foot edema test). The compounds of the invention are also active when administered dermally. Such topical activity has been measured by means of the guinea pig erythema test and by a contact sensitivity test. Antiinflammatory activity can also be detected by other assays known to the art such as the cotton pellet granuloma test and the adjuvant arthritis test. Analgesic activity has been observed using standard test methods such as the phenylquinone writhing (mouse) and Randall-Selitto (rat) tests.

Leading references to the rat foot edema method are:
(1) Adamkiewicz et al, *Canad. J. Biochem. Physiol.*, 33:332 (1955);
(2) Selye, *Brit. Med. J.*, 2:1129 (1949); and
(3) Winter, *Proc. Exper. Biol. Med.*, 111:544 (1962).

The edema test is performed on adult female rats. Generally, one group of 10 rats serves as non-medicated controls, while another group of 10 rats receives the test compound at various times prior to the induction of the edema, usually 15 minutes, one hour and/or 18 hours. The test compound is administered orally as a suspension in a 4 percent aqueous solution of acacia. Edema is induced by the plantar injection of 0.5 percent carrageenin (0.1 ml/foot) into the right hind foot. The left hind foot receives a like volume of 0.9 percent saline solution. Three hours later, the volume of each hind foot is determined plethysmographically. The edema is expressed as the increase in the volume of the edemogen injected foot less the volume of the saline injected foot. The percent inhibition is calculated by dividing the mean increase in the edema of the medicated group by the mean increase in the edema of the non-medicated group, subtracting this quotient from 1, and multiplying the resulting number by 100. An active dose is that giving a statistically significant inhibition of the induced edema, usually in the range of at least about 25-35 percent inhibition. The preferred compounds of the invention shown in Examples 1, 3, 4, and 7 below exhibit 56 percent, 77 percent, 74 percent, and 85 percent inhibition, respectively, in the above test at doses of 100 mg/kg.

The compounds of the invention preferably are administered orally but other known methods of administration can also be used, e.g., dermatomucosally (for example dermally, rectally and the like), parenterally (for example by subcutaneous injection, intramuscular injection, intraarticular injection, intravenous injection and the like), and by ocular administration. Effective dosages should be less than a toxic amount. Such dosages ordinarily fall within the range of about 1 to 500 mg of the compound of the invention per kg of body weight of the mammal to be treated. Oral dosages are usually below 100 mg/kg. The compounds of the invention ordinarily are administered in the form of compositions containing the compound together with a pharmaceutically acceptable carrier. Suitable compositions for oral administration are in the form of liquids (such as 4 percent acacia and polyethylene glycol solutions), tablets (which can contain anhydrous lactose, microcrystalline cellulose, modified starch, calcium stearate and talc, as well as other conventional compounding agents together with the active antiinflammatory agents), solid suspensions and capsules. Pharmaceutically acceptable carriers for topical application include creams, gels, tapes and the like. Liquid formulations, such as solutions or suspensions of the active ingredient in inert carriers, can be used for dosage by injection.

Using the methods described above, the preparation of compounds of the invention is illustrated in the following examples. The purpose of the examples is to enable those skilled in the art to practice the invention, and they are not intended to limit in any way the scope of the invention.

EXAMPLE 1

Preparation of a Compound wherein L is Carbonyl, Using Process C

Step 1

To a stirred solution of 4-bromo-2,6-di(t-butyl)phenol (1218 g, 4.27 mole) and 4 kg of dry glyme was added 4.27 mole of n-butyl lithium. To this mixture was added 4.3 mole of trimethylsilyl chloride. A solid precipitated. The mixture was allowed to stand for about 16 hours, then filtered. The filtrate was evaporated and the residue was dissolved in a mixture of dichloromethane and water. The organic layer was separated and dried. Evaporation provided a residue which was washed with diethyl ether. The product was 2,6-di(t-butyl)-4-bromotrimethylsilylphenol, in the form of light yellow needles.

Alternate Step 1

To a mixture of 142.6 g (0.50 mole) of 4-bromo-2,6-di(t-butyl)phenol and 200 ml of dry acetonitrile was added 115 g of bis(trimethylsilyl)acetamide. The reaction mixture was heated on a steam bath for 15 hours with a reflux condenser. The reflux mixture was evaporated to provide a residue which was recrystallized from hexane and then from petroleum ether to provide white solid 2,6-di(t-butyl)-4-bromotrimethylsilylphenol. This structure was confirmed by infrared and nuclear magnetic resonance spectral analysis.

Step 2

The Grignard reagent of 2,6-di(t-butyl)-4-bromotrimethylsilylphenol was prepared by reacting 0.10 mole of 2,6-di(t-butyl)-4-bromotrimethylsilylphenol with 0.12 mole of magnesium turnings in tetrahydrofuran. The reaction was initiated by adding a few crystals of iodine. The mixture was heated at its reflux temperature for 4 hours to provide the desired Grignard reagent.

Step 3

To a solution of 10 g (0.093 mole) of pyridine-3-carboxaldehyde in 25 ml of tetrahydrofuran was added a solution of the Grignard reagent prepared in Step 2 in 250 ml of tetrahydrofuran. The reaction mixture was heated to its reflux temperature and maintained at reflux for about 4 hours. The reflux mixture was adjusted to a pH of 5 with 10 percent hydrochloric acid and then extracted with dichloromethane. The extracts were dried and evaporated to provide a residue. This residue was triturated with hexane and cooled to −20° C. to provide a fine precipitate. The precipitate was separated by filtration and washed with petroleum ether. The product was 1-(3'-pyridyl)-1-(3,5-di(t-butyl)-4-trimethylsiloxyphenyl)methanol.

Step 4

To a solution of 10 g of sodium dichromate dihydrate in 100 g of dimethylsulfoxide was added a solution of 2.0 g of the product of Step 3 in about 60 ml of dimethyl sulfoxide. This mixture was stirred until all of the solid was dissolved, and 1.2 ml of concentrated sulfuric acid was then added thereto. The acidified mixture was heated on a steam bath for 1 hour. The heated mixture was poured into excess 10 percent hydrochloric acid and extracted twice with benzene. The benzene extracts were separated and dried, then evaporated to provide a residue which was recrystallized from benzene and triturated with petroleum ether to provide a solid product. Recrystallization from a benzene:hexane mixture provided 2,6-di(t-butyl)-4-nicotinoylphenol, m.p. 143.5°–144.5° C.

| Analysis: | % C | % H | % N |
| --- | --- | --- | --- |
| Calculated for $C_{20}H_{25}NO_2$: | 77.1 | 8.1 | 4.5 |
| Found: | 77.5 | 8.3 | 4.5 |

EXAMPLE 2

Preparation of a Compound wherein L is Carbonyl, Using Process C

To a mixture of 16.1 g (0.15 mole) of pyridine-4-carboxaldehyde in 50 ml of tetrahydrofuran was added a solution of a Grignard reagent made from 0.15 mole of 2,6-di(t-butyl)trimethylsilylphenol in 250 ml of tetrahydrofuran. The mixture was heated at its reflux temperature for 16 hours. The reflux mixture was acidified with 10 percent hydrochloric acid, then basified with concentrated ammonium hydroxide. The resulting solution was extracted with chloroform and the organic layer was dried. The organic layer was evaporated to provide a solid. The solid was rinsed with petroleum ether. The resulting product was 1-(4'-pyridyl)-1-(3,5-di(t-butyl)-4-trimethylsiloxyphenyl)methanol.

To a solution of 8.0 g of this product and 100 ml of dry acetone was added 50 ml of a solution of 10 percent chromic acid prepared by dissolving sodium dichromate in aqueous sulfuric acid. The resulting mixture was heated on a steam bath for 1 hour. The pH of the heated mixture was adjusted to 10 with dilute sodium hydroxide solution. The resulting basic solution was extracted with dichloromethane repeatedly until the dichloromethane extract was colorless. These extracts were dried over magnesium sulfate and evaporated, yielding a residue. To the residue was added petroleum ether with scratching, resulting in crystallization of a solid product. The product was recrystallized from petroleum ether to provide 2,6-di(t-butyl)-4-(4'-pyridinecarbonyl)phenol, in the form of tan needles, m.p. 171°–172.5° C.

| Analysis: | % C | % H | % N |
| --- | --- | --- | --- |
| Calculated for $C_{20}H_{25}NO_2$: | 77.1 | 8.1 | 4.5 |
| Found: | 77.3 | 8.1 | 4.4 |

EXAMPLE 3

Preparation of a Compound wherein L is Carbonyl, Using Process D[1]

To a solution of 20.82 g (0.2 mole) of 2-cyanopyridine in 100 ml of tetrahydrofuran was added 250 ml of a solution of 0.21 mole of the Grignard reagent prepared from 4-bromo-2,6-di(t-butyl)trimethylsilylphenol. The mixture was heated at reflux for 48 hours. To this mixture was added 200 ml of 20 percent hydrochloric acid solution. This mixture was heated at reflux for 4 hours. The pH of the reaction mixture was adjusted to 8 by adding aqueous sodium hydroxide solution. The aqueous layer was separated and extracted with dichloromethane. This dichloromethane extract was added to the tetrahydrofuran layer and the organic layers then dried. The organic layers were evaporated to provide an oily semisolid. The residue was rinsed with a mixture of benzene and heptane, and a product was obtained by recrystallizing twice from heptane with treatment with decolorizing charcoal. The resulting product was 2,6-di(t-butyl)-4-(2'-pyridinecarbonyl)phenol, in the form of tan needles, m.p. 154°–156° C.

| Analysis: | % C | % H | % N |
|---|---|---|---|
| Calculated for $C_{20}H_{25}NO_2$: | 77.1 | 8.1 | 4.5 |
| Found: | 77.3 | 8.2 | 4.5 |

EXAMPLES 4–5

Preparation of Compounds wherein L is Carbonyl, Using Process $D^1$ and Process $D^2$ Using the method of Example 3, compounds of the invention were prepared from various cyanopyridines and 4-bromo-2,6-di(t-butyl)trimethylsilylphenol. Purification by recrystallization and column chromatography was used to obtain the product compounds. The example numbers, cyanopyridine intermediates, resulting products, and melting point of the products are shown below in Table I.

TABLE I

| Example No. | Cyanopyridine Intermediate | Product | Melting Point (in °C.) |
|---|---|---|---|
| 4 | 3-methyl-2-cyanopyridine | 2,6-di(t-butyl)-4-(3'-methyl-2'-pyridinecarbonyl)phenol | 116.5–117.5 |
| 5 | 4-cyanopyridine | 2,6-di(t-butyl)-4-(4'-pyridinecarbonyl)phenol | 171–172.5 |

EXAMPLE 6

Preparation of a Quaternary Ammonium Salt of the Compound of Example 3

To a mixture of 8.0 g (0.0257 mole) of 2,6-di(t-butyl)-4-(2'-pyridinecarbonyl)phenol in 150 ml of ethanol was added 3.7 g (0.0257 mole) of methyl iodide. The solvent was allowed to evaporate, resulting in formation of a residue. The residue was dissolved in hot ethanol and hexane added thereto, then the resulting solution was cooled and scratched to provide crystals of bright yellow 2-(3',5'-di(t-butyl)-4'-hydroxybenzoyl)-1-methylpyridinium iodide, m.p. 198°–200° C. (dec.).

| Analysis: | % C | % H | % N |
|---|---|---|---|
| Calculated for $C_{21}H_{28}INO_2$: | 55.6 | 6.2 | 3.1 |
| Found: | 55.5 | 6.3 | 2.9 |

EXAMPLE 7

Preparation of a Compound wherein L is a Carbon-Carbon Bond, Using Process B

Step 1

A solution of 200 g (1.625 mole) of picolinic acid and 176.2 g (0.80 mole) of 2,6-di(t-butyl)benzoquinone in 1 liter of cymene was heated at its reflux temperature for 16 hours under a nitrogen atmosphere. The reaction mixture was extracted twice with 5 liters of 10 percent hydrochloric acid. The acid layers were basified with concentrated sodium hydroxide solution and the basic layer was extracted with dichloromethane. The dichloromethane layer was dried over magnesium sulfate, then evaporated to a dark solid. The solid was washed with petroleum ether to provide 2,6-di(t-butyl)-4-hydroxy-4-(2'-pyridyl)-2,5-cyclohexadien-1-one, in the form of an off-white solid.

Step 2

A solution of 10 g (0.033 mole) of 2,6-di(t-butyl)-4-hydroxy-4-(2'-pyridyl)-2,5-cyclohexadien-1-one in ethanol was placed in a Parr apparatus with 0.1 g of Raney nickel and reduced until the hydrogen pressure decreased from 0.31 MPa to 0.29 MPa. The catalyst was removed by filtration and the solvent was evaporated, resulting in formation of a residue. The residue was washed with hexane, then recrystallized from hexane to provide white 2,6-di(t-butyl)-4-(2'-pyridyl)phenol, m.p. 125°–127° C.

| Analysis: | % C | % H | % N |
|---|---|---|---|
| Calculated for $C_{19}H_{25}NO$: | 80.5 | 8.8 | 4.9 |
| Found: | 80.9 | 8.9 | 4.7 |

The reduction of Step 2 was also carried out by an alternative method as shown below in Alternate Step 2.

Alternate Step 2

To a stirred solution of 5 g (0.0167 mole) of 2,6-di(t-butyl)-4-hydroxy-4-(2'-pyridyl)-2,5-cyclohexadien-1-one in 100 ml of diethyl ether was added excess lithium aluminum hydride. Stirring was continued for 30 minutes after completion of the exotherm. The stirred mixture was treated carefully with a mixture of ethanol, water and 10 percent hydrochloric acid to hydrolyze the mixture. The aqueous layer was separated, neutralized with dilute sodium hydroxide solution, and extracted with dichloromethane. The extracts were dried, then evaporated to provide a residue which was suspended in petroleum ether. The residue gradually crystallized. The structure was determined to be 2,6-di(t-butyl)-4-(2'-pyridyl)phenol by infrared and nuclear magnetic resonance spectral analysis and comparison with the compound of Step 2.

EXAMPLE 8

Preparation of a Compound wherein L is a Carbon-Carbon Bond, Using Process B

Using the method of Example 7 (Step 1 and Alternate Step 2) and starting with 4-methylpicolinic acid the white solid product 2,6-di(t-butyl)-4-(4'-methyl-2'-pyridyl)phenol, m.p. 132.5°–135.5° C. was prepared.

Various modifications and alterations of this invention will be apparent to those skilled in the art without departing from the scope and spirit of this invention and the latter should not be restricted to that set forth herein for illustrative purposes.

What is claimed is:

1. A compound of the formula:

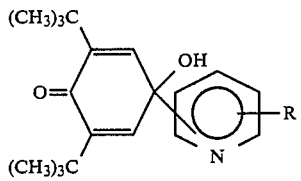

wherein R is hydrogen or methyl.

2. A compound according to claim 1, wherein R is hydrogen.

* * * * *